United States Patent [19]

Delente

[11] Patent Number: 5,104,803
[45] Date of Patent: Apr. 14, 1992

[54] PHOTOBIOREACTOR

[75] Inventor: Jacques Delente, Kensington, Md.

[73] Assignee: Martek Corporation, Columbia, Md.

[21] Appl. No.: 163,800

[22] Filed: Mar. 3, 1988

[51] Int. Cl.[5] ............................................. C12M 1/00
[52] U.S. Cl. .................................. 435/287; 435/313;
435/314; 435/316; 47/1.4; 362/101
[58] Field of Search ............... 435/257, 287, 289, 290,
435/313, 314, 316, 284, 285; 422/186, 186.3;
47/1.4; 250/432 R, 494.1; 362/101, 240, 267,
375

[56] References Cited

U.S. PATENT DOCUMENTS

| | | | |
|---|---|---|---|
| 2,273,449 | 2/1942 | Plishker | 250/494.1 |
| 2,815,607 | 12/1957 | Schroeder | 47/58 |
| 3,705,576 | 12/1972 | Roth | 250/494.1 X |
| 3,986,297 | 10/1976 | Ichimura et al. | 47/1.4 |
| 4,253,418 | 3/1981 | Lockwood et al. | 47/1.4 X |
| 4,302,545 | 11/1981 | Redikultsev et al. | 435/289 |
| 4,373,024 | 2/1983 | Hunt | 435/314 X |
| 4,676,956 | 6/1987 | Mori | 435/289 X |

FOREIGN PATENT DOCUMENTS

| | | |
|---|---|---|
| 0084325 | 7/1980 | European Pat. Off. . |
| 0103729 | 3/1984 | European Pat. Off. . |
| 6057041 | 12/1980 | Japan . |
| 0113883 | 7/1982 | Japan ............... 250/432 R |
| 2040282 | 2/1987 | Japan ............... 435/287 |
| WO86/05201 | 9/1986 | PCT Int'l Appl. ........ 435/287 |
| 0953631 | 8/1982 | U.S.S.R. ............... 435/289 |

OTHER PUBLICATIONS

Richard Radmer, Paul Behrens and Kathleen L. Arnett, "An Analysis of the Productivity of a Continuous Algal Culture System", *Biotech & Bioeng.*, 29, 1987, pp. 1-26.

Y. K. Lee—"Enclosed Bioreactors for the Mass Cultivation of Photosynthetic Microorganisms: the Future Trend"; *Tibtech*, Jul. 1986, pp. 186-189.

Mori, "Value-Added Solar Ray Supply System", *Expert*, Aug. 1983, pp. 94-99.

Mori et al., "Sunlight Supply System and Gas Exchange in Microalgal Bioreactor System", *Adv. in Space Res.*; 1986 (McElroy and Shoog, eds) Pergammon Press 1987.

*Primary Examiner*—Robert J. Warden
*Assistant Examiner*—William H. Beisner
*Attorney, Agent, or Firm*—Rothwell, Figg, Ernst & Kurz

[57] ABSTRACT

The present invention relates to a photobioreactor for the cultivation of photosynthetic micoorganisms having at least one light bank substantially totally immersible in the liquid microbial culture contained in the photobioreactor so that substantially all of the emitted light is absorbed in the culture. The light bank comprises a plurality of light tubes in substantially close proximity to each other, electrical leads extending from the light tubes to a source of electric power and an enclosure means enclosing at least the portions of the electrical leads into the lead tubes to render such points impervious to the liquid microbial culture. The light bank serves as a light source as well as may be arranged to form channels for the circulation of the liquid culture within the photobioreactor.

22 Claims, 4 Drawing Sheets

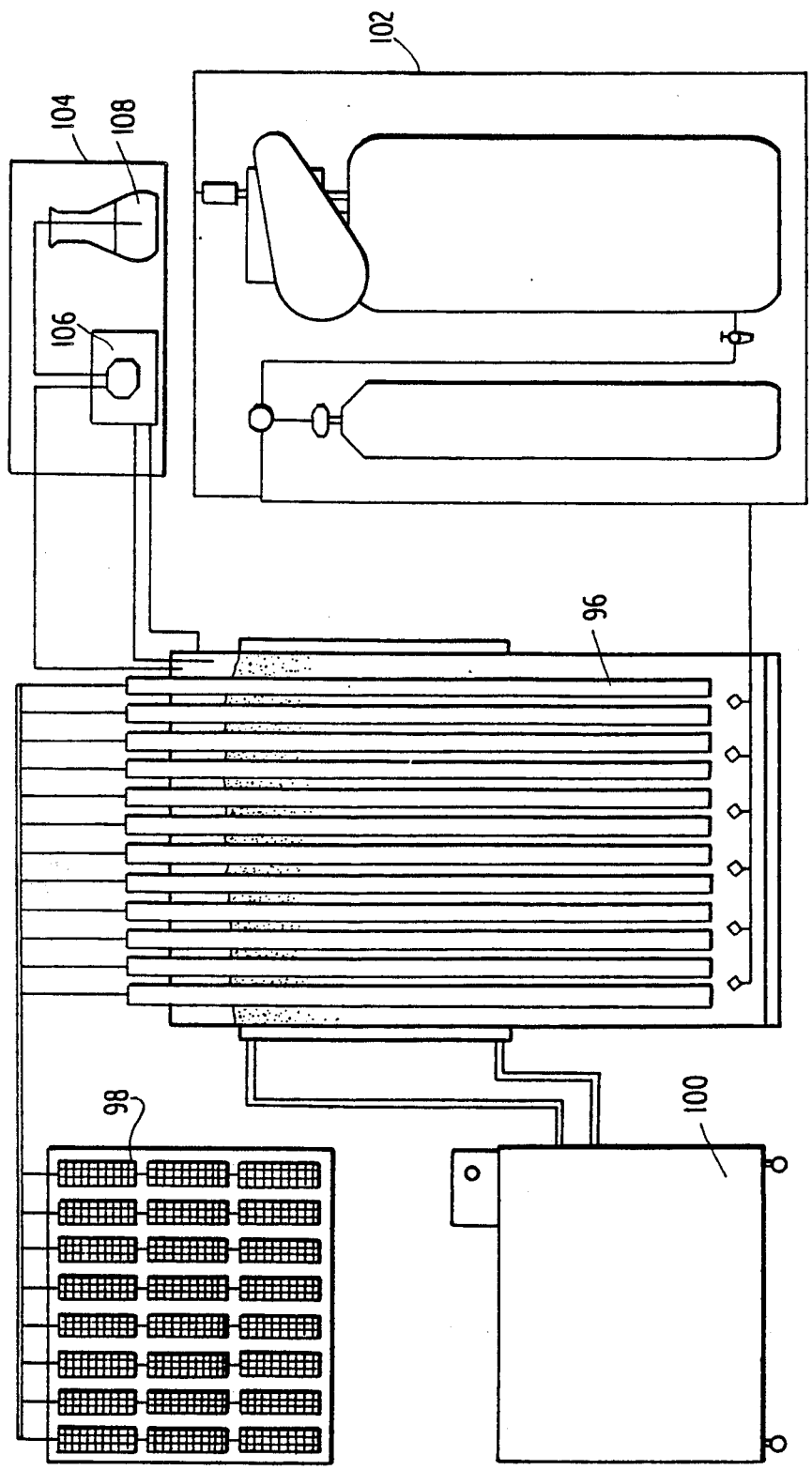

PHOTOBIOREACTOR

BACKGROUND OF INVENTION

Algae have been cultivated artificially for such diverse purposes as the production of food for animals and humans, the treatment of sewage and waste waters, and the accumulation of radioactive wastes. More recently, algal cultures have been used for the production of enzymes having industrial and research applications and for producing oils and other materials having nutritional value. Modern biotechnology offers an opportunity for the genetic modification of algae to yield cultures capable of producing a wide variety of useful materials.

Various methods and equipment have been employed for the artificial culturing of algae. Perhaps the simplest procedures have involved the use of shallow open ponds exposed to sunlight. Such ponds are subject to contamination by dust, other microorganisms, insects and environmental pollutants and provide minimal ability to control the degree of exposure to light, temperature, respiration and other important factors. A more sophisticated approach has involved growing algal cultures in plastic-covered trenches and ponds, optionally having electrically powered pumps and agitators. These configurations reduce the chances of contamination of the culture and permit more accurate control of temperature, respiration and other parameters. Such configurations are still quite inefficient in terms of providing adequate and uniform amounts of light to the algal cells, particularly when sunlight is the sole source of light.

Unlike other microorganisms, the nutrient requirements of algae are very inexpensive; carbon dioxide being the principal source of carbon. On the other hand, the photosynthetic process requires that the algae be exposed to a relatively constant and uniform source of light. A primary design factor for modern photobioreactors involves providing a means for uniformly exposing the cells in the algal culture to the optimum amount of visible light. Like many plants, algae are quite sensitive to the amount and kind of light. Excessive light intensity can damage and kill algal cells. Too little light results in low levels of photosynthesis.

A number of design factors are affected by the means selected for supplying light to the cells. For example, light sources, including natural sunlight, often emit substantial amounts of heat. Algal cultures are sensitive to heat, and many of them grow most efficiently at relatively low temperatures (e.g., about 27° C.). Thus, means must often be provided for cooling the algal culture and dissipating heat generated by the light source.

Two design factors closely related to the requirement for a uniform and constant supply of light are the cell density and the light path length. Like conventional fermentation processes, it is usually desirable to use as high a cell density as possible Many of the same considerations apply to algal cultures as to bacterial cultures. For example, in addition to the light requirements, one must take into account the competition for nutrients, respiratory demands, viscosity and pumpability of the culture medium, and the like. An extremely high cell density results in cells more than a few millimeters from the light source being effectively shielded from the light. Simply increasing light intensity will not overcome this problem, because highly intense light will damage or kill cells near the light source.

The only effective way of increasing cell densities while maintaining a uniform amount of light is to employ a relatively short light path length. Of course, the requirement that the photobioreactor have a relatively short light path length introduces a new set of design problems. For industrial applications, it is usually desirable to employ high-volume microbial cultures. Large culture volumes are amenable to continuous or large-scale batch recovery operations and generally result in economies of scale. Satisfying the requirements for large culture volumes and short light path lengths has required that the photobioreactor have large, transparent walls which are closely spaced to define a light path and a fluid chamber within which the algal culture is contained. The transparent walls are illuminated with an appropriate light source to sustain the growth and photosynthetic reactions of the cells.

Various designs of such photobioreactors have been employed. A relatively simple design which has been successfully used in laboratory and pilot plant operations is simply a glass chamber having large, flat, parallel side walls and a narrow bottom and end walls. A gas sparging tube is placed in the bottom of the chamber to allow carbon dioxide or carbon dioxide-enriched air to be sparged through a culture medium contained in the chamber, and banks of fluorescent light tubes are arranged adjacent to the exterior of the side walls of the chamber. Inocula, nutrients, buffers, and the like can be introduced into the chamber through the top which may optionally be covered with a lid. This design has been very successful and useful for small scale operations.

An alternative embodiment of a bioreactor employing a fluorescent tube involves a cylindrical culture chamber having glass walls which surround a single fluorescent tube. The culture chamber may also be surrounded by a concentric cylindrical water jacket for controlling the temperature of the culture. Such a photobioreactor is described by Radmer, R., Behrens, P., and Arnett, L., "An Analysis of the Productivity of a Continuous Algal Culture System, *Biotechnology and Bioengineering*, 29 (1987), pp. 488–492. This design has also proven very valuable for laboratory-scale algal culturing operations, but, for many of the reasons described above, has not proven particularly useful for large-scale operations.

Thus, in recent attempts to design large-scale photobioreactors, attention has been focused on devising efficient means for distributing light uniformly, and in the correct intensity, across large transparent walls of the reactor.

Various photobioreactor designs are reviewed in an article by Yuan-Kun Lee, "Enclosed Bioreactors for the Mass Cultivation of Photosynthetic Microorganisms: The Future Trend," *TIBTECH*, July 1986, p. 186–189. A significant need still exists for large-scale photobioreactors capable of using high intensity, low-cost lamps which are physically remote from the liquid culture medium to minimize electrical hazards and transfer of heat from the lamps to the culture medium.

SUMMARY OF THE INVENTION

The present invention comprises a novel photobioreactor in which at least one and preferably a plurality of light banks are mounted side by side in a tank containing a liquid microbial culture. The banks are positioned in the tank so that the light emitting surfaces thereof are substantially totally immersed in the liquid. Each of the light banks is made up of a plurality of light tubes, preferably fluorescent lamps, in close proximity to one another with their longitudinal axis lying generally in the same plane. The light bank includes an enclosure means enclosing at least the portions of the electrical leads and light tubes to render these portions impervious to the liquid microbial culture when immersed in the culture. Electrical leads are connected to the electrical contacts of the light tubes and extend from the bank to allow connection to external electrical power source.

The entire light-emitting structure of the light bank can thus be immersed in the liquid microbial culture. Spacing between adjacent light tubes as well as between adjacent light frames is such as to optimize transmission of the emitted light to the algae.

The light banks also perform a structural function through the direct utilization of the external surfaces of the light banks as walls or draft spaces to define circulation paths through which the algae is moved by means such as air lift agitation. The light banks also form basic building blocks or modules which can be used in combination in any desired number for large scale photobioreactor systems of any selected capacity. Spacing between the light tubes in each bank and between banks may be selected to provide any desired length of light path.

The invention allows, among other things, more efficient and more economical use of fluorescent light tubes, while at the same time utilizing the light banks themselves as part of the structure of the photobioreactor to define circulation paths for the algae culture.

In addition, electrical circuitry and connections are greatly simplified, reducing installation and maintenance costs as well as risks of short circuits.

BRIEF DESCRIPTION OF DRAWINGS

FIG. 6 is a schematic of a algal production system including the photobioreactor of the present invention.

DETAILED DESCRIPTION OF THE INVENTION

Figure 1:
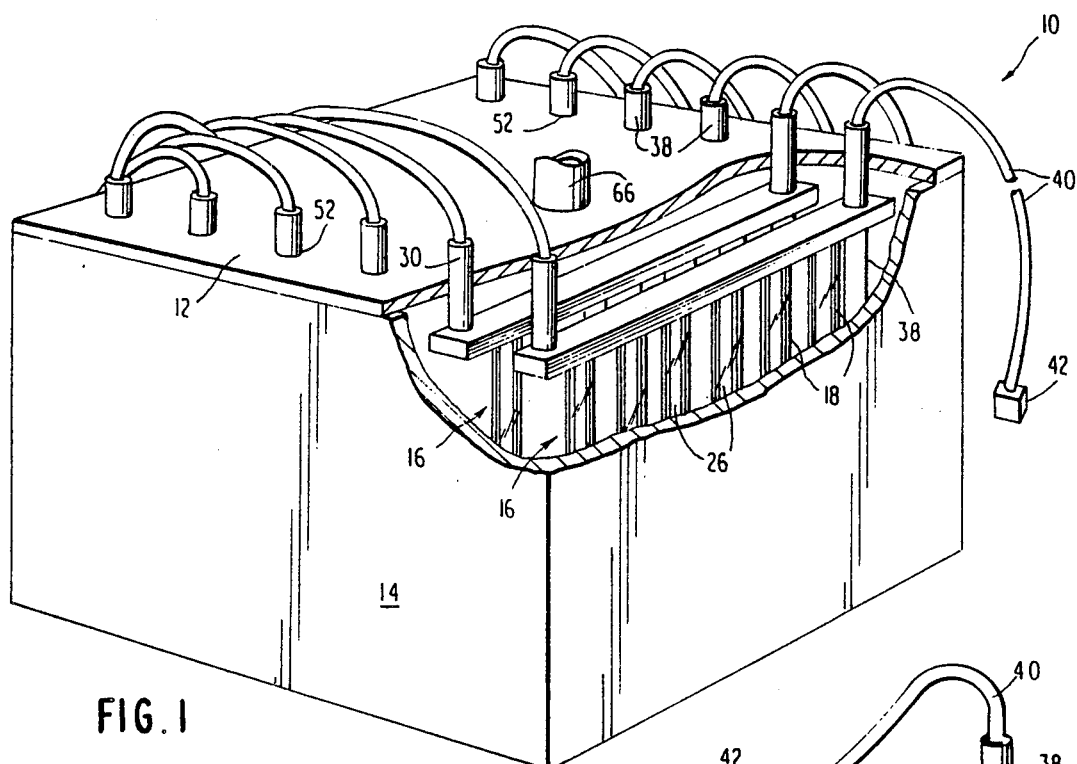
FIG. 1 is perspective view of a photobioreactor illustrating one embodiment of the present invention.

Referring now to the drawings, FIG. 1 is a perspective view of a photobioreactor 10 illustrating one embodiment of the present invention. A portion of the cover 12 of the reactor is shown cut away to permit illustration of a portion of the interior of the reactor. The exterior of the reactor 10 is in the form of a tank 14 capable of containing a liquid culture medium. The liquid culture medium is sometimes referred to as an "algal" culture, but it will be appreciated that the photobioreactor 10 may be employed for the cultivation of any type of photosynthetic microorganism.

The tank 14 may be of any convenient shape but for the embodiment illustrated in FIG. 1, a generally flat-sided, rectangular or cube shape is preferred.

Located within the reactor 10 is a series of light banks 16 which are positioned and supported within the reactor in a manner later to be described. Electrical connections to the light banks are made through a series of tubular pipes 18 made preferably of an electrically insulating and chemically inert material such as methyl methacrylate, polycarbonate and the like. Extending through the pipes 18 are portions 40 of wiring harnesses terminating in plugs 47 for connecting the light banks 16 to an electrical power source.

Figure 2:
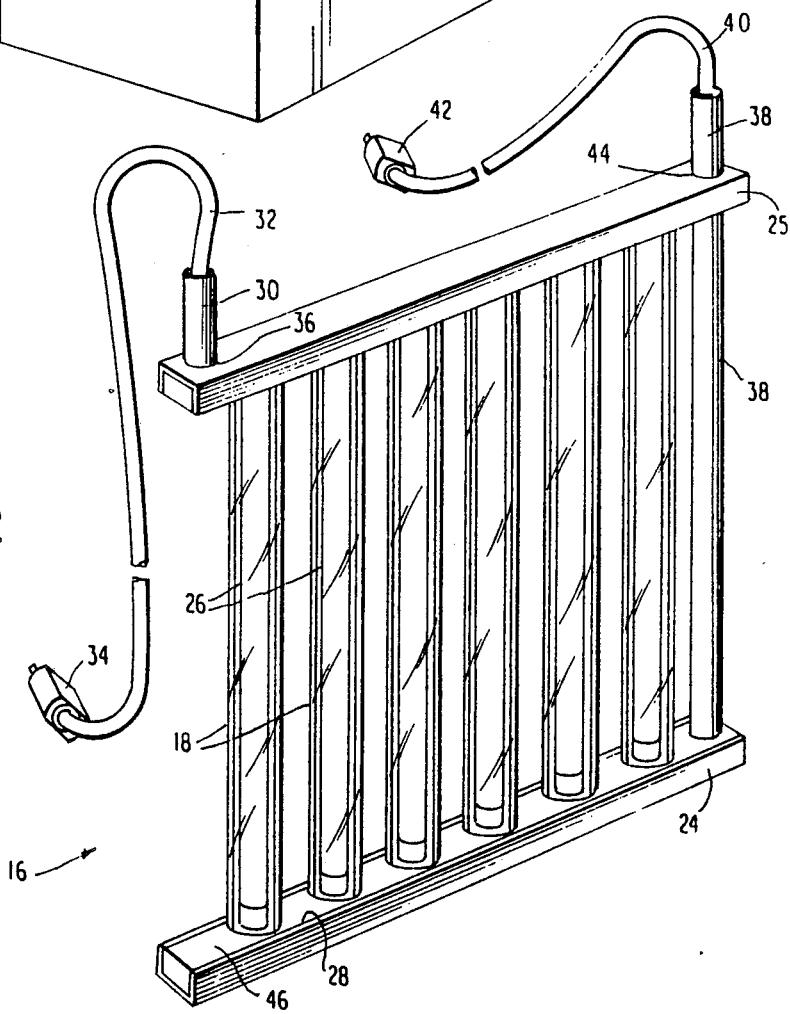
FIG. 2 is a perspective view of a light bank illustrating one embodiment of the present invention and forming a part of the photobioreactor of FIG. 1.

FIG. 2 is a perspective view of one of the light banks 16 according to one embodiment and is partially illustrated in FIG. 1. The light bank 16 is formed of a pair of spaced apart, generally elongated channel members 24 and 25 made of a chemically inert material such as plexiglass having a series of light tubes 26 extending therebetween. As will be later explained in further detail, the light bank 16 comprising the two channel members 24 and 25 and the light tubes 26 forms an integral, self-contained structure which is light weight and easily portable and which can be used in any desired number in a large scale photobioreactor system.

In the embodiment shown in FIG. 2, the light tubes 26 are fluorescent tube lamps used essentially in their commercial "off the shelf" condition without any modifications or customization. The advantages of such lamps in this embodiment is that light is emitted from them substantially uniformly along the length of the tubes and in all directions perpendicular to the tubes 26.

Electrical connection to the light tubes 26 are made at their opposite ends in the conventional, well known way and suitable ballasts (not shown) are provided as well. These connections are all made within recesses 28 formed by the channel members 24. In order to make the electrical connections, twelve electrical leads are required in each channel.

The leads connected to the light tubes 26 through the upper channel member 24 are brought out through a pipe 30 and are enclosed in a preferably flexible sheath 32 which terminates in an electrical plug connectible to a source of electrical power. The pipe 30 is formed of an electrically insulating chemically inert material and is secured to and sealed around its periphery at the point of entry 36 to the upper channel member 25 by any well known technique.

The leads connected to the light tubes 26 through the lower channel member 24 are brought out through a pipe 38 which extends from lower channel 24 through upper channel 25 and is secured to and sealed around its periphery at the point of entry 44 to the upper channel 25, again by any well known technique. The leads from the lower channel 24 are enclosed in a preferably flexible sheath 40 connectible to an electrical power source. When both plugs 34 and 42 are connected to an electrical power source, circuits through the light tubes 26 are completed and the light tubes are energized and caused to emit light.

As stated above all of the electrical connections to the light tubes 26 themselves are made within the recesses 28 formed within channel members 24 and 25.

These connections, along with the exposed connector portions of the light tubes 26, are all encased in enclosure means 46 which totally encloses the electrical leads and the connector portions of the light tubes 26 at the points of entry of the electrical connectors into the light tubes and renders these portions impervious to the liquid microbial culture in which the light frame 16 is to be immersed. In the embodiment shown in FIG. 2, the enclosure means 46 is preferably formed of a potting compound which is poured into the channel member recesses 28 and cured in place to a dense, impervious mass. The potting compound may, for example, be a silicone resin sold by General Electric under the designation RTV 615 or it may be any other suitable compound having similar characteristics.

The enclosure means 46 may also be formed in other ways such as, for example by an enclosure member made of plexiglass or similar material placed over the channel recesses 28 and sealed in place to the channel members 24 and 25 and to the outer surfaces of the light tubes 26. It has been found however, that the potting compound approach shown in FIG. 1 forms an acceptable enclosure structure over the electrical connections at the points of entry to the light tubes 26 such that these areas rendered impervious to liquid microbial cultures, thus allowing the light frame 16 along with the entire light emitting portions of the light tubes 26 to be totally immersed in the liquid culture.

The distance between the outer surfaces of the light tubes 26 mounted in close proximity to one another with their longitudinal axes lying generally in the same plane as in FIG. 2 is selected to optimize light transmission to the algal culture in the tank when a light bank is submerged in a photobioreactor. The optimum spacing for the light paths formed between the light tubes 26 will vary depending upon the type of culture used and the cell density. For algal cultures where shorter light paths are preferred, the distance between the outer surfaces of adjacent lamps within the light bank will generally be from about 0 to 3 centimeters. In general, however, the light paths for such cultures will range from 0.5 to 50 centimeters.

Figure 3:
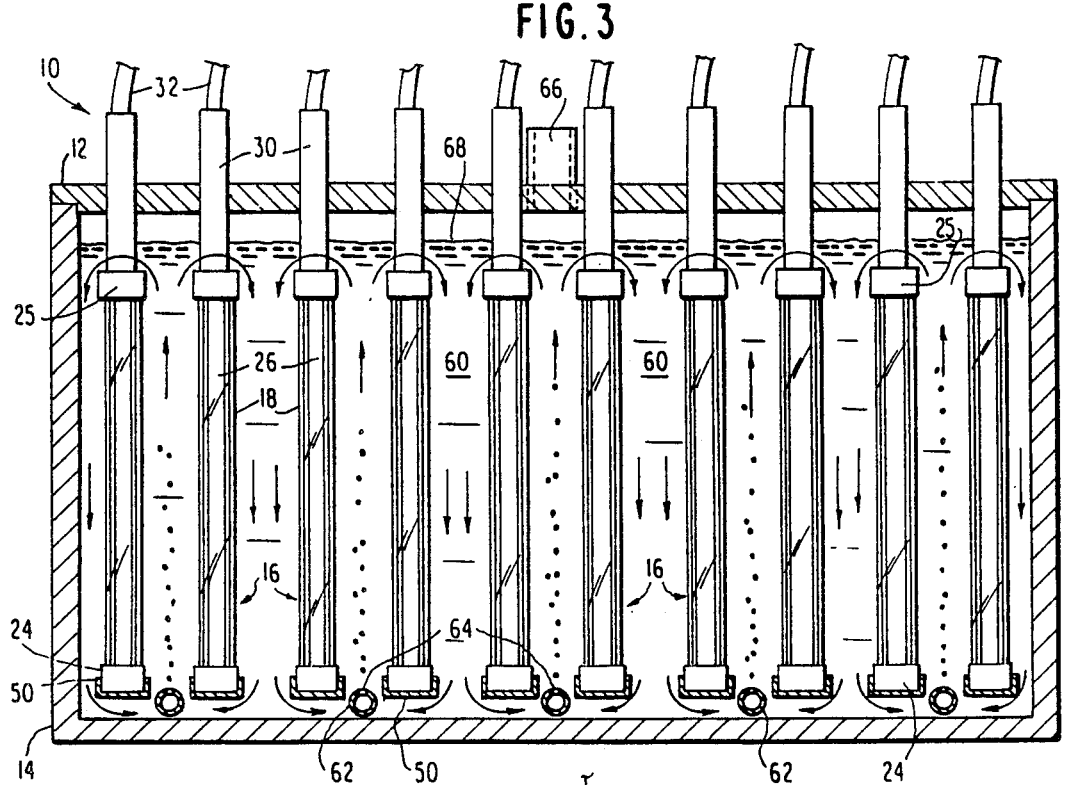
FIG. 3 is a cross sectional view of a photobioreactor in which a portion of the wall of the side of the tank is shown cut away in order to illustrate the interior portion of the photobioreactor.

According to another embodiment of the present invention, as shown in FIG. 3, in which a portion of the side of the tank 14 is shown cut away in order to illustrate an interior portion thereof, light banks 16 are mounted with the lower channel members 24 thereof supported in brackets 50 which extend between and are supported on the side walls of the tank 14. The tubes 30 and 38 which extend from the upper channel members 25 extend through apertures 52 in the cover 12 as shown in FIGS. 1 and 3. If the cover 12 is to be sealed to the tank 14, the tubes 30 and 38 would also be sealed to the cover 12 at the apertures 52.

The light banks 16 are mounted in the tank 14 forming passages 60 therebetween for circulation of the algal culture to enhance the growth process. In order to promote the circulation and agitation of the algal culture within the tank a series of hollow tubes or cylinders 62, preferably formed of a metal or ceramic material, are placed between alternate pairs of the light banks 16 as shown in FIG. 3. The cylinders 62 contain small perforations or apertures 64 extending through the walls thereof. The cylinders 62 form gas sparging tubes through which a pressurized gas (e.g., carbon dioxide or carbon dioxide-enriched air) is supplied for supporting the photosynthesis requirements of the algal culture. Gas bubbles rise through the liquid algal culture and escape through an exit tube 66 located above the surface level of the culture medium.

The movement of the gas bubbles up through the culture medium causes circulation of the culture medium through the passages 60 in the directions shown by the arrows in FIG. 3. This enhances the growth of the algal culture. Other means for supplying nutrient source gases and for circulating the culture may, of course, be used.

It is important to note, however, that the light banks 16, in addition to supplying light to the algal culture, also structurally form the passages or draft spaces 60 between the banks for circulation of the culture medium.

As shown in FIG. 3, the light banks 16 are totally immersed in the algal culture which has a normal operating liquid level 68. As stated above, the spacing of adjacent light tubes 26 in each row of the light banks 16 is selected to optimize light transmission to the algal culture being grown. Similarly the spacing A between the light banks 16 as mounted in the tank and illustrated in FIG. 3 is selected for optimum light absorption based on the same considerations. Generally, algal cultures suited for optimum growth in short light path environments will utilize a space A of about 1 to 3 centimeters.

Because of the total immersion in the liquid culture of the light emitting surfaces of the light tubes 26 and by reason of the proper selection of the light path lengths as described above, virtually 100% of the emitted light is absorbed by the algal culture and the light absorption is relatively uniform and optimized throughout the culture as well. The electrical leads connected to the ends of the light tubes 26 are completely shielded and rendered impervious to the liquid culture 70 at the points of entry into the light tubes by reason of enclosure means such as within the channel members 24 and 25.

Figure 4:
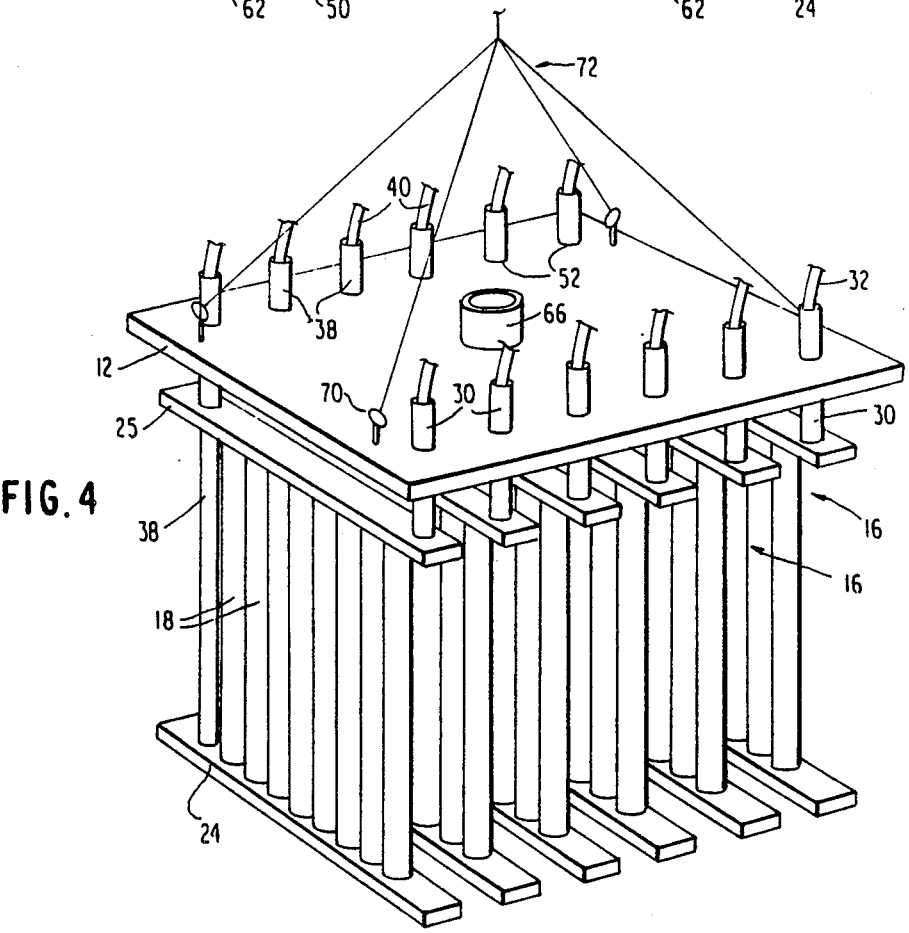
FIG. 4 is a perspective view of a cover of the reactor illustrating one embodiment of the present invention.

According to another embodiment as illustrated in FIG. 4, the light banks 16 are attached to the cover 12, such as in the area of the tubes 30. The means for attachment 74 includes pins, latches, etc. One advantage of this embodiment is the ease of removal of the light banks 16 for cleaning, maintenance, etc. The cover 12 may contain a number of apertures 52 through which the tubes 30 may pass. In order to remove the cover 12, eyelets 70 may be used to connect suitable overhead means 72 to vertically remove the cover 12 and light banks 16 attached thereto.

The light banks 16 may be formed in shapes other than that selected for the embodiment illustrated. For example the light tubes 26 may be mounted in a circular path instead of in a straight line is shown in FIG. 2. In such a configuration, the centerlines of the light tubes would form a circle when viewed in a direction parallel to the tube axes. This shape would be more suitable for a cylindrical tank where a single, circularly shaped light frame may be used or a number of concentrically positioned light frames used for larger configurations. In such a configuration, the peripheral length of each light frame is greater as the distance from the center of cylindrical tank increases and a single interchangeable modular design can not be used. However, the other advantages of this invention as described herein are still realized in such alternate configurations.

Figure 5:
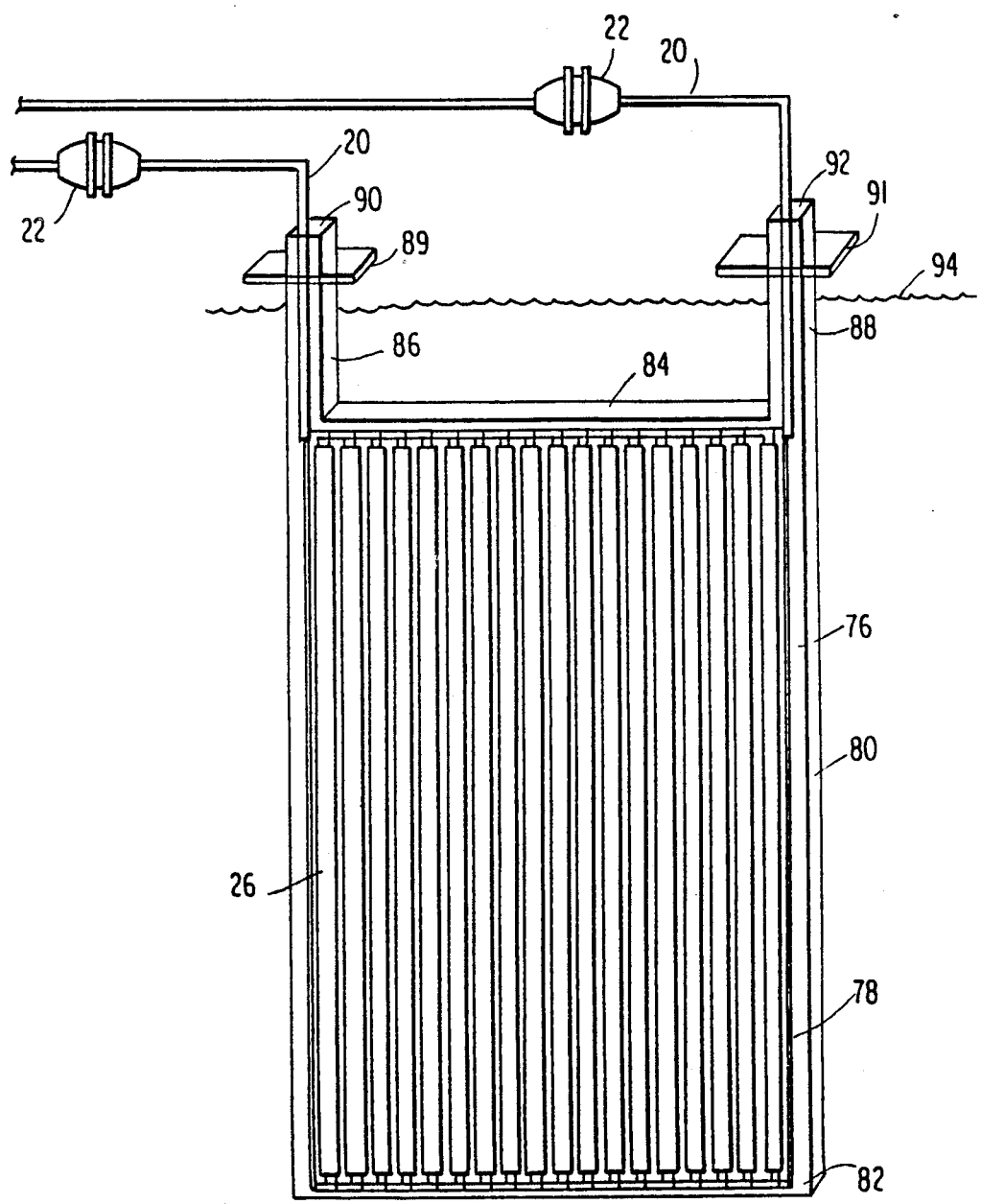
FIG. 5 is a partially schematic side view of a light bank according to one embodiment of the present invention and containing a plurality of light tubes which are contained in a water-tight compartment surrounding all of the light tubes in the light bank.

In the most preferred embodiment of the present invention as shown in FIG. 5, the enclosure means for the light tubes 26 and the portions of the electrical leads for the light bank 16 comprises a water-tight compartment 76. The compartment 76 is constructed of light frame of electrically insulating and chemically inert material such as methyl methacrylate, polycarbonate and the like. The outer side walls of the compartment 76 must be of a material which will allow the transmission of light to the liquid microbial cultures while being impervious to the aqueous environment. The water-tight compartment 76 has generally flat, transparent side walls 78 and 80 and end walls 82 and 83 in sealed attachment to the side walls 78 and 80. The water-tight compartment has a bottom wall 85 and top wall 86 in sealed attachment to the side walls 78 and 80.

The thickness of the walls of the compartment 76 may vary so long as sufficient strength is provided to the light assembly for ease of removal and cleaning. In a preferred embodiment, the walls 78, 80, 82, 83, 85 and 86 of the water-tight compartment 76 have a thickness of from 1/16" to ½" with a thickness of ¼ being particularly preferred. The side walls may be thinner than the remaining walls with the thickness of 1/16" being particularly preferred. With the decreased thickness in the side walls 78 and 80, the hydrostatic pressure is better distributed within the bioreactor. In the most preferred embodiment, the side walls 78 and 80 have sufficient flexibility that when exposed to hydrostatic pressure in the photobioreactor, the side walls 78 and 80 actually contact and partially conform to the shape of the light tubes 26.

The upper portions of the light bank 87 and 88 are designed to pass through the apertures 52 in the cover 12. The upper portions of the light bank 87 and 88 may be attached to the cover 12 by a variety of means known to those skilled in the art, including latches, pins, etc. and as shown in FIG. 4. The top of the compartment for the light bank contains at least one aperture 90 and preferably a second aperture 92 through which portions 20 of the electrical harness may pass. While in use, the upper level of liquid microbial media 94 should be maintained below apertures 90 and 92 and preferably at a level where foaming of the media can be tolerated.

To insure a good seal of the contents so as to avoid their loss to the environment through an aperture 52, the light bank 16 preferably has a sealing means for the space that may exist between aperture 52 and upper portions 87 and 88. Suitable sealing means 89 and 91 may consist of a panel or gasket material which abutts the bottom of the cover 12.

According to the most preferred embodiment as shown in FIG. 5, the light bank 16 is impervious to the aqueous environment, thus protecting the fluorescent light tubes 26 and cleaning of the light bank 16 is simplified by simply wiping down the sides of the water-tight compartment 76. Another advantage of this preferred embodiment is the electrical connections to the fluorescent light tubes 26 need not be sealed in upper and lower channels 24, 25, so long as the electrical connections are contained within the water-tight compartment 76.

FIG. 6 schematically illustrates an algal production system including the photobioreactor 96 of the present invention, an electrical supply 98 for the photobioreactor 96, a means 100 for controlling the temperature of the contents within the photobioreactor, a means 102 for production of air and $CO_2$, and an antifoaming system 104.

Various means for controlling the temperature of the contents in the photobioreactor 96 are known to those skilled in the art and include a heating unit and/or refrigeration unit. A preferred means for controlling the temperature also includes water jackets 105 which can be connected to the temperature control unit 98.

The water jackets 105 are plumbed such that any of the water jackets 105 may be bypassed, if desired. Preferably, there are a total of five water jackets, one on the tank bottom and one on each of the four sides. The water jackets mounted on the sides are internally buffed to increase the heat transfer rate.

Air may be supplied to the photobioreactor 96 by a compressor 106 and carbon dioxide by cylinders 108. These two gas streams are mixed in a gas proportion to give the desired enriched gas, i.e., two percent carbon dioxide. The means for producing the air and $CO_2$ 102 are connected to spargers 62.

The antifoam system 104 may be a pump 110 and antifoam supply 112. A number of means for activation of the pump 110 is contemplated such as detecting the resistance cross to leads wherein one lead is attached to the tank and the other is suspended above the culture serving as a probe.

While it is thus apparent that the preferred embodiment shown and described provides certain advantages, many of the advantages of the present invention can nevertheless be realized in other configurations, and it will be appreciated that various modifications, changes and adaptions can be made, all of which are intended to be comprehended within the meaning and range of equivalents of the appended claims.

We claim:

1. A photobioreactor comprising:
   (a) a tank for containing a liquid microbial culture at a preselected operating level within said tank;
   (b) a plurality of modular light banks within said tank, each of said plurality of modular light banks comprising:
      (i) a plurality of light tubes, wherein each of said light tubes has ends with electrical contacts, a longitudinal axis and an outer light emitting surface, said light tubes being arranged in close proximity to one another so that the outer light emitting surfaces are separated by a predetermined distance and the longitudinal axes of the light tubes are substantially parallel and lie generally in a plane;
      (ii) electrical leads connected to the ends of each of said light tubes for connection to a source of electrical power; and
      (iii) an enclosure means forming a water-tight compartment surrounding the light tubes, wherein said enclosure means comprises;
         generally flat, transparent side walls which are substantially parallel to one another and to the plane of the longitudinal axes of the light tubes, and which are in close proximity to the light tubes,
         end walls extending in the direction of the longitudinal axes of the light tubes and in sealed attachment to the side walls,
         a bottom wall in sealed attachment to the side walls and the end walls, and
         a top wall, with at least one aperture through which the electrical leads pass, in sealed attachment to the side walls and end walls; and
   (c) support means constructed and arranged so as to support and position said modular light banks within said tank in adjacent, spaced apart and substantially parallel relation to each other with a periodic preselected distance between adjacent banks such that when said tank is filled with a liquid microbial culture at the preselected operating level, substantially the entire light emitting surfaces of said light tubes are immersed in said culture and substantially all of the light emitted from said light tubes is transmitted into the culture.

2. The photobioreactor as set forth in claim 1 in which said light tubes are fluorescent tube lamps.

3. The photobioreactor as set forth in claim 1 in which the predetermined distance between the outer light emitting surfaces of the light tubes within the modular light banks is from about 0 to about 3 centimeters.

4. The photobioreactor as set forth in claim 1, further including a gas introduction means positioned and arranged so as to introduce a sparging gas between at least some of the modular light banks.

5. The photobioreactor as set forth in claim 1, in which the preselected distance between adjacent modular light banks is from about 1 to about 3 centimeters and in which the predetermined spacing between the outer light emitting surfaces of the light tubes within the modular light banks is from about 0 to about 3 centimeters.

6. The photobioreactor as set forth in claim 1, wherein said support means is further constructed and arranged so as to cover a top opening of the tank.

7. The photobioreactor as set forth in claim 1, wherein the side walls of said enclosure means have sufficient flexibility so that when exposed to hydrostatic pressure in the photobioreactor, said side walls will contract and partially conform to a shape of said light tubes.

8. The photobioreactor as set forth in claim 1, wherein the side walls of said enclosure means have a thickness ranging from about 1/16" to about ½".

9. The photobioreactor as set forth in claim 8, wherein the side walls of said enclosure means have a thickness of 1/16".

10. The photobioreactor as set forth in claim 1, wherein said side walls, said end walls, said bottom wall, and said top wall are made of methyl methacrylate or polycarbonate.

11. The photobioreactor as set forth in claim 1, wherein said tank has a plurality of side walls and said support means is further constructed and arranged so as to be in communication with said plurality of tank side walls.

12. The photobioreactor as set forth in claim 1, further comprising an electrical supply connected to said electrical leads, temperature control means constructed and arranged so as to control the temperature of the culture within said tank, gas supply means constructed and arranged so as to introduce gas into said tank, and antifoaming means constructed and arranged so as to prevent the formation of foam within said tank.

13. The photobioreactor as set forth in claim 12, wherein said temperature control means comprises a heating unit and cooling unit in fluid communication with at least one water jacket located on at least one side of said tank.

14. A light bank for a photobioreactor which comprises:
(i) a plurality of light tubes, where each of said light tubes has ends with electrical contacts, a longitudinal axis and an outer light emitting surface, said light tubes being arranged in close proximity to one another so that the outer light emitting surfaces are separated by a predetermined distance and the longitudinal axes of the light tubes are substantially parallel and lie generally in a plane;
(ii) electrical leads connected to the electrical contacts of each of said light tubes for connection to a source of electrical power; and
(iii) an enclosure means forming a water-tight compartment surrounding the light tubes, wherein said enclosure means comprises;
generally flat, transparent side walls which are substantially parallel to one another and to the plane of the longitudinal axes of the light tubes, and which are in close proximity of the light tubes,
end walls extending in the direction of the longitudinal axes of the light tubes and in sealed attachment to the side walls,
a bottom wall in sealed attachment to the side walls and the end walls, and
a top wall, with at least one aperture through which the electrical leads pass, in sealed attachment to the side walls and end walls.

15. The light bank for a photobioreactor as set forth in claim 14 wherein the side walls of said enclosure means have sufficient flexibility so that when exposed to hydrostatic pressure in the photobioreactor, said side walls will contact and partially conform to a shape of said light tubes.

16. The light bank for a photobioreactor as set forth in claim 14, in which said light tubes are fluorescent tube lamps.

17. The light bank for a photobioreactor as set forth in claim 14, in which the predetermined distance between the outer light emitting surfaces of the light tubes within the light banks is from about 0 to about 3 centimeters.

18. The light bank for a photobioreactor as set forth in claim 14, wherein said at least one aperture comprises two apertures.

19. The light bank for a photobioreactor as set forth in claim 14, wherein the side walls of said enclosure means have a thickness ranging from about 1/16" to about ½".

20. The light bank for a photobioreactor as set forth in claim 19, wherein the side walls of said enclosure means have a thickness of 1/16".

21. The light bank for a photobioreactor as set forth in claim 14, wherein said side walls, said end walls, said bottom wall, and said top wall are made of methyl methacrylate or polycarbonate.

22. A photobioreactor comprising:
(a) a tank for containing a liquid microbial culture at a preselected operating level within said tank;
(b) a plurality of compartment forming means positioned within said tank in adjacent, parallel relation to each other and having a periodic spacing with respect to each other, each of said compartment forming means comprising generally flat optically transparent side walls;
(c) a light bank within said each of said compartment forming means, said light bank comprising a plurality of light tubes supported and positioned within said compartment forming means in substantially close proximity with each other;
(d) means for sealing said compartment forming means against fluid communication with the interior of said tank; and
(e) each of said compartment forming means being positioned within said tank such that substantially all light emitted from said light tubes is transmitted to said culture when said tank contains said culture at said preselected operating level.

* * * * *

UNITED STATES PATENT AND TRADEMARK OFFICE
CERTIFICATE OF CORRECTION

PATENT NO. : 5,104,803
DATED : April 14, 1992
INVENTOR(S) : Jacques Delente

It is certified that error appears in the above-identified patent and that said Letters Patent is hereby corrected as shown below:

On the cover, add inventors Paul W. Behrens and Richard J. Radmer.

Col. 1, line 60, "possible Many" should be --possible. Many--

Col. 5, line 22, after "areas" insert --are--.

Col. 6, line 49, "is" should be --as--.

Col. 7, line 43, "abutts" should be --abuts--.

Col. 9, line 14, "the" should be --said--.

Col. 9, line 29, "contract" should be --contact--.

Signed and Sealed this

Sixth Day of June, 1995

Attest:

BRUCE LEHMAN

*Attesting Officer*  *Commissioner of Patents and Trademarks*